United States Patent [19]

Welch

[11] 4,359,447

[45] Nov. 16, 1982

[54] AUTOMATIC MULTICHANNEL APPARATUS FOR PERFORMING EMERGENCY ANALYSES, IN PARTICULAR CHEMICAL-CLINICAL ANALYSES ON BIOLOGICAL FLUIDS

[76] Inventor: Henry H. Welch, No. 1262, Via Tiburtina Km. 12.600, 00131, Rome, Italy

[21] Appl. No.: 222,181

[22] Filed: Jan. 2, 1981

[30] Foreign Application Priority Data

Jan. 7, 1980 [IT] Italy .............................. 47531 A/80

[51] Int. Cl.³ .................... G01N 35/06; G01N 21/11; G06F 15/42
[52] U.S. Cl. ........................................ 422/63; 422/64; 422/67
[58] Field of Search ............................ 422/67, 63, 64; 364/497, 498

[56] References Cited

U.S. PATENT DOCUMENTS

| | | | |
|---|---|---|---|
| 3,728,080 | 4/1973 | Moran | 422/67 |
| 3,778,790 | 12/1973 | Prost et al. | 422/67 X |
| 3,917,455 | 11/1975 | Bak et al. | 422/67 X |

*Primary Examiner*—Michael S. Marcus
*Attorney, Agent, or Firm*—Beveridge, Degrandi & Kline

[57] ABSTRACT

The invention relates to an automatic multichannel apparatus for performing emergency analyses on biological fluids comprising an arm carrying a needle arranged for taking out the sample directly from a test tube, a rotating distributing arrangement suitable for dividing the aspirated sample in a number of parts corresponding to the number of desired analyses, means for the addition of reagents, a unit for performing photometric measurements, and means for data transmission to a microprocessor or a computer for the processing of said data and the printout of the results.

14 Claims, 6 Drawing Figures

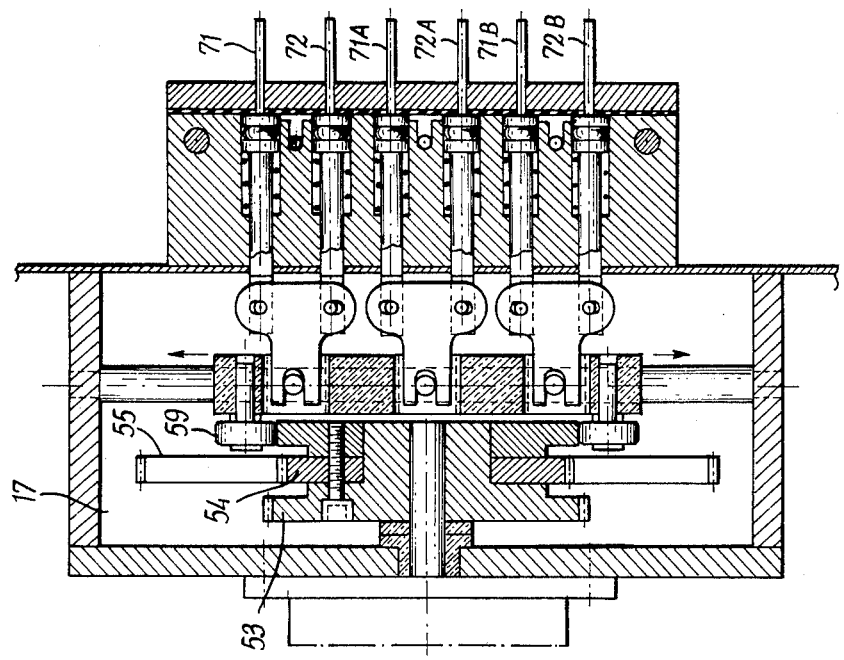
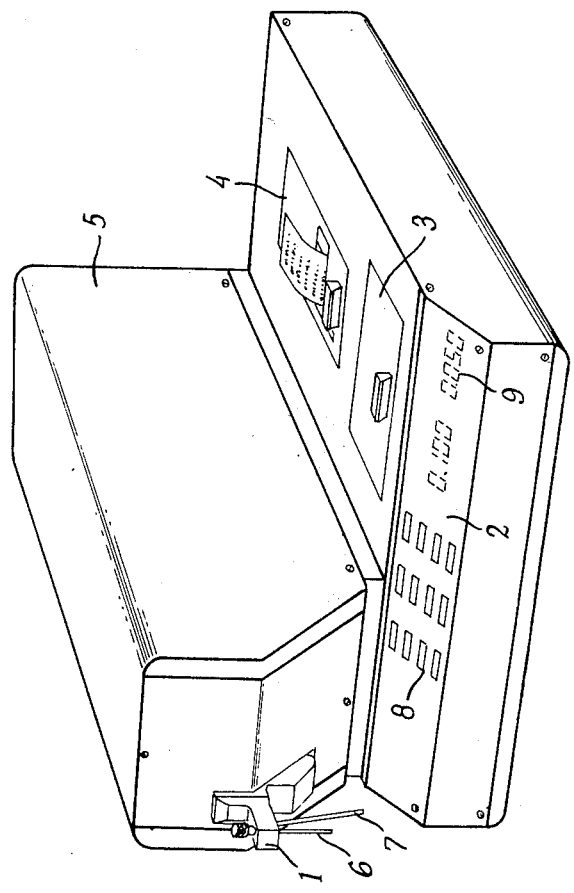

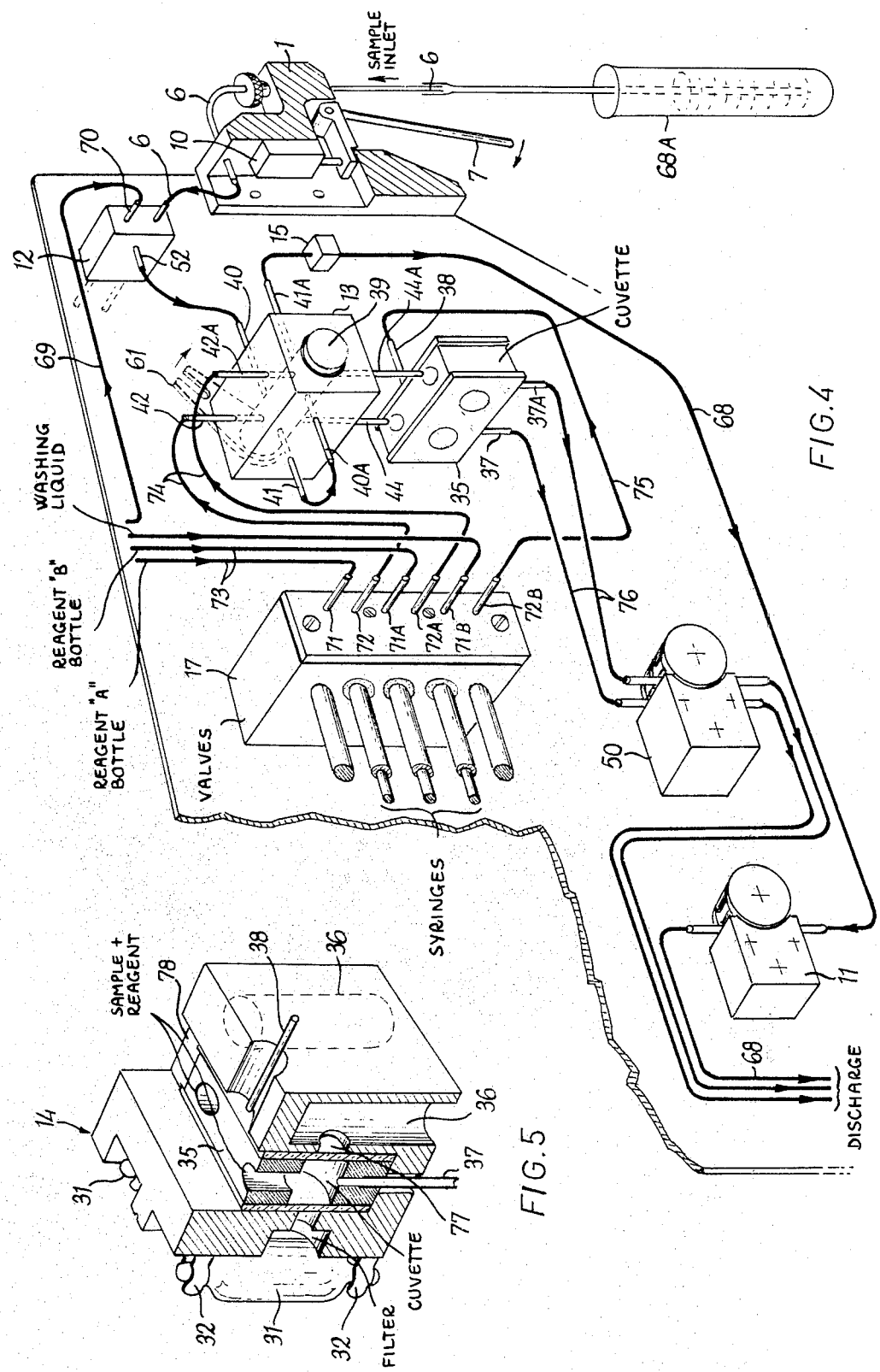

AUTOMATIC MULTICHANNEL APPARATUS FOR PERFORMING EMERGENCY ANALYSES, IN PARTICULAR CHEMICAL-CLINICAL ANALYSES ON BIOLOGICAL FLUIDS

The present invention relates to an automatic multichannel apparatus for performing analyses on fluids, in particular chemical-clinical analyses on biological fluids.

More in particular the invention relates to a multichannel apparatus which permits effecting from two to thirty or more different analyses at the same time on the same sample of liquid being tested. Specifically, the invention relates to an apparatus for performing quickly and accurately a number of different analyses on a fluid sample or a group of fluid samples.

With the development and the wide-spread use of preventive medicine and of a greater control of patients in hospitals, it has become necessary to perform a greater number of analyses of a different kind for each patent. Consequently, an automatic apparatus which permits performing different kinds of analyses at the same time on the same sample has become indispensable, particularly in the case of emergency analyses. Moreover, with the great increase of the single analysis of a different type for each patient, there is also the big problem of the recordal of the data coming from the several kinds of apparatus or different departments or laboratories, where the possibility of a human error increases with the greater number of analyses to be performed and of results to be recorded.

The present invention provides also an apparatus which allows the identification of the sample with a complete control performed by a microprocessor, the printout of the results being also included. There is also considered the connection with a computer arranged with particular interfaces and programs specifically designed for the purpose, for performing a complete patient data sheet.

The main purpose of the present invention is to provide an automatic multichannel apparatus, which is able to perform with great precision and speed a large number of analyses of a different kind at the same time or simultaneously on the same sample, from two upwards. This system not only automates each of the subsequent steps of the processes actually used analytical and clinical chemistry, but introduces also features of simplicity and flexibility which allow the utilization of non specialized technicians. It eliminates old manual methods, transcription or record errors, allows the utilization of specialized man power or technicians, and offers to modern technology results and data which are more precise and impossible to obtain with manual operations.

Another purpose of the invention is to provide an automatic multichannel apparatus for analyses of fluids in which each sample is discretely handled in its cuvette eliminating possibilities of errors or contamination.

A further purpose of the invention is the one of providing a multichannel system which permits obtaining results for one up to thirty or more different analyses at the same time and within a time span which goes from one to three minutes. This permits use of the apparatus also for emergencies in hospitals.

Another purpose of the invention is the one of providing a system which uses microquantities of sample and microquantities of reagent for reducing the costs.

Another purpose of the invention is to provide a system which is able to perform a single or several analyses simultaneously according to the needs of the patient.

According to the invention there is provided an apparatus comprising in combination, an arm carrying a needle arranged for aspirating the sample directly from the test tube, a rotating distributor associated with an arrangement of syringes having the duty of aspirating and dispensing reagents, and means for measurement and for washing.

The sample is aspirated by said distributor according to a segmented passage, in such a quantity so as to perform all the analyses (up to thirty or more). Each segment represents one analysis. The capacity of the segment corresponds to the volume of the sample to be analysed. The segment is washed by a precise quantity of a specific reagent within a suitable cuvette provided with thermostatic control wherein the chemical reaction and the photometric measurement are performed. The data of the several measurements are transferred to a microprocessor or to a computer which performs the processing and the printout of the result.

After the handling of each sample the whole system is washed before aspirating the next sample in order to avoid contamination.

The invention will be now disclosed with reference to the attached drawings, which represent as a non-limiting example a preferred embodiment of the invention itself.

In the drawings:

FIG. 1 is a perspective view of the apparatus according to the invention;

FIG. 4 is a perspective view which shows how the connections are arranged;

FIG. 5 shows details of the photometric system with a cuvette in a perspective section;

FIG. 6 represents a section made along line VI—VI of FIG. 2 of the arrangement of valves and for the supply of reagents.

Figure 2:
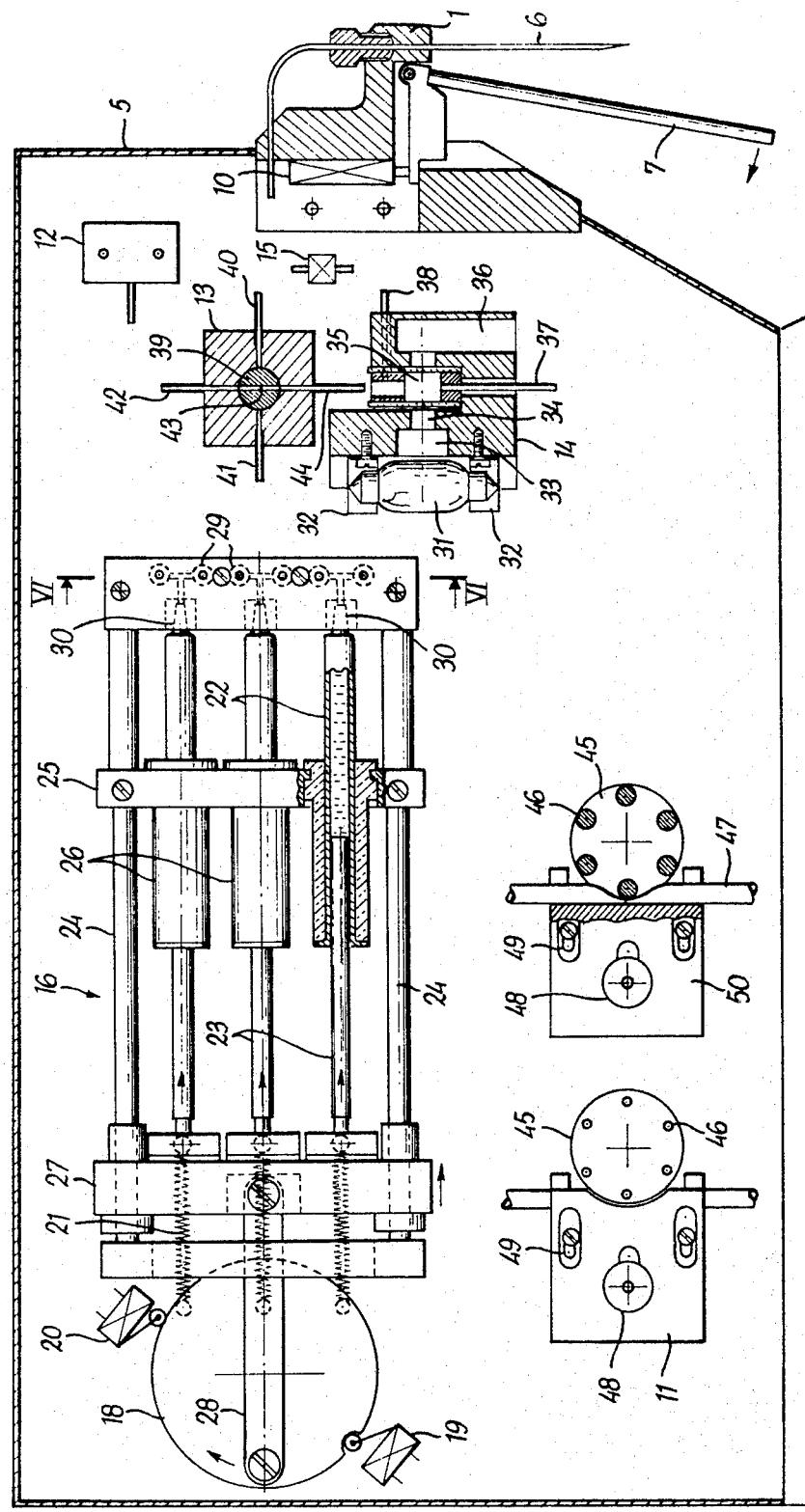
FIG. 2 represents a side view with the lid and several parts which are represented in section.

With reference to FIG. 1, the apparatus comprises an arm 1 carrying a tube, the control panel 2, a door 3 for commands, the printer 4 with associated microprocessor and the case 5.

The arm 1 carries a tube 6 through which the liquid to be analyzed is aspirated.

By actuating the microswitch control 7 a peristaltic pump is energized which causes the aspiration in of the sample to be analysed. The tube 6 may be associated with a self-propelled arm of a sampler operating automatically and containing the samples to be analyzed, disclosed in other patents in the name of the same applicant.

On the control panel 2 there are indicated the several operations and controls with lamps 8. In this way, the several analyses which are performed may be identified; these being in a number identical to the number of analyses and/or operations or checks which the apparatus may perform at the same time. These lamps 8 are lighted according to the analyses which are performed or to indicate the operations and the necessary checks. The digital displays 9 indicate the results of the analyses (two or more at the same time) which at the same time are printed on the printer 4.

Behind the door 3 there are arranged the several controls necessary for the operative surveillance, such as the energization or the disengagement of the apparatus, the manual or automatic operation, the check of the washing at the end of the work day.

In FIG. 2 there is shown a side view with the lid and some parts which are shown in section. There are shown arm 1 carrying tube 6, the microswitch control 7 and the microswitch 10, which energizes the peristaltic pump 11 which aspirates the sample to be analyzed, the switching valve 12, which rates at one time the sample to be analyzed and thereafter the washing water for eliminating the contamination. There are also shown the system 13 for the metering of the samples, the photometric system 14, the electronic sensor 15, the system 16 for the supply of reagents and the washing comprising syringes, the valve system 17, the cam 18 for the actuation of the syringes, the microswitches 19 and 20, the springs 21 for the restoration of the syringes in their initial positions, the syringes 22 with the respective pistons 23. These pistons are fastened to the support 27 which slides on the guides 24, by means of the connecting rod 28, whilst the sleeves 26 are blocked by the support 25. The terminating parts of the syringes 22 are housed in the housings 30 communicating with the opening and closure valves 29.

The photometric system 14 comprises a light source 31, with suitable lamp carriers 32, an interference filter 33, a lens 34, a microcuvette 35, a detector 36, a tube 37 for the discharge of the cuvette, a tube 38 through which the liquid for washing the microcuvette is supplied after each analysis.

The system for the metering of the sample to be analyzed indicated at 13, comprises a rotating distributor 39 provided with holes as indicated in 39, which is movable within the body of metering system 13; the sample to be analyzed is aspirated through the inlet 40 and eliminated through the small outlet tube 41. After that the distributor 39 is rotated through 90 degrees, and the reagent of one of the syringes 22 forces the reagent through the inlet 42, transferring the aspirated sample into the segment 43 and the reagent through the outlet 44, into the microcuvette 35.

The peristaltic pump 11 comprises a motor which rotates the wheel 45 within which the dowels 46 are mounted, which squeeze a pliable tube 47, which in turn aspirates the sample to be analyzed. The knob 48 permits adjusting the distance between the body of the pump 11 and the tube 47 with respect to the dowels 46. Guides 49 permit a smooth displacement. The peristaltic pump 50 is a pump which permits the insertion of two tubes 47 for aspirating simultaneously two liquids, consequently there are two housings for two tubes 47. Its operation is identical to the one of the pump 11.

The array of syringes 16 is arranged for delivering the reagents and/or the washing fluid into the cuvette. A motor rotates the cam 18, whose connecting rod 28 pushes the support 27 along the guides 24 forcing the pistons 23 of the syringes 22 to the expulsion stroke for expelling the fluid through the valves 29 into the inlet 42, the springs 21 restore the pistons 23 of the syringes to the intake stroke and these latter are again filled with reagents derived from suitable external reservoirs. The switching for aspirating and dispersing of the syringes is controlled by the valves 29.

Figure 3:
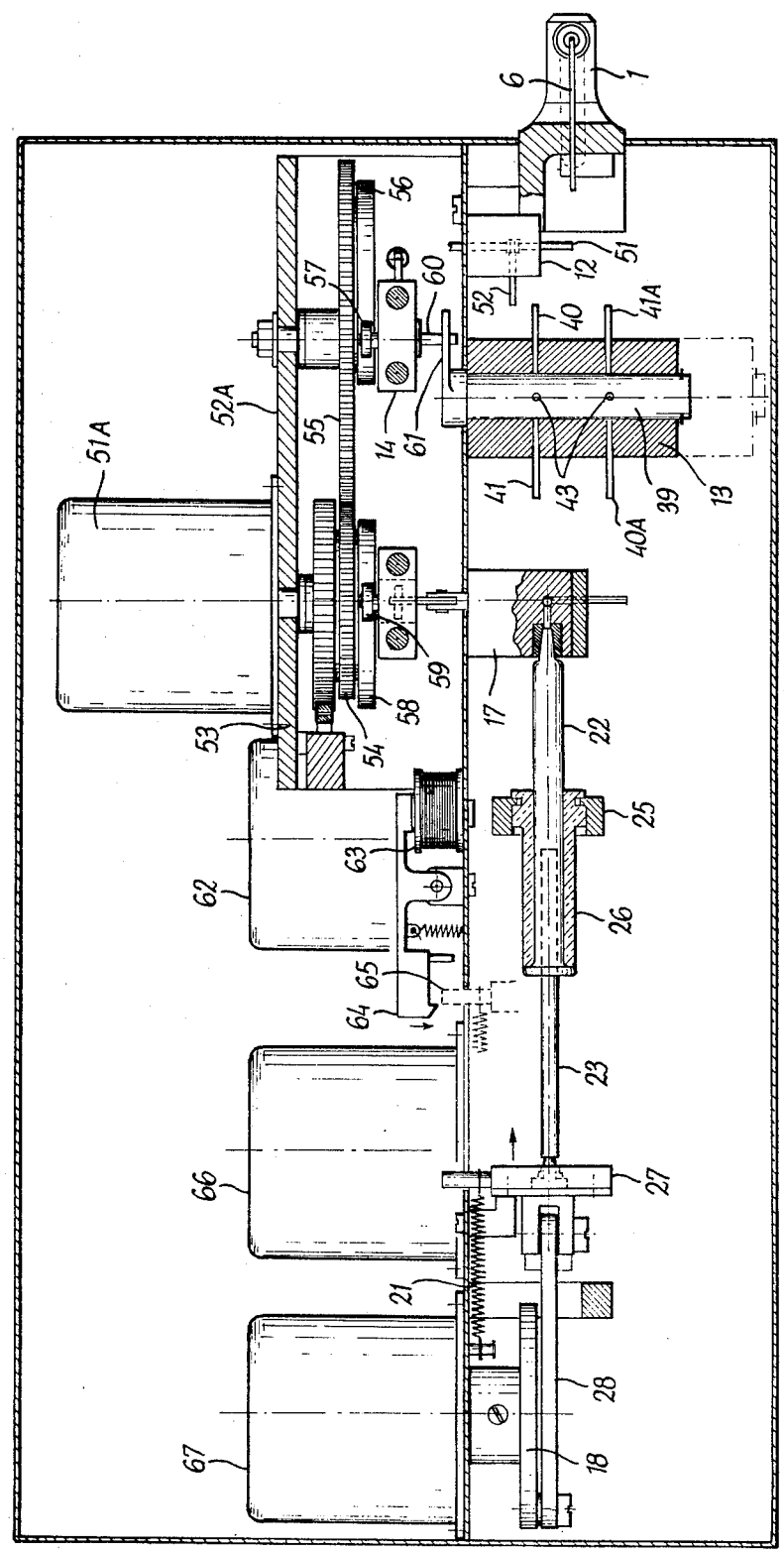
FIG. 3 is a top view showing the mechanical parts, with some parts being shown in section.

FIG. 3 is a top view, with some parts shown in section, of the mechanical unit. The tube carrier or arm 1 along with the tube 6 is connected with the switching valve 12. The sample to be analyzed is aspirated in through the inlet 51 and comes out from the outlet 52, entering into the system 13 for the metering of the sample, through the inlet 40 and comes out from the outlet 41, entering again into the inlet 40A and coming out from the outlet 41A, as many times as the number of different analyses which are performed at the same time. The substantially cylindrical part of rotating distributor 39 contains a number of segments 43 or quantities of liquid to be analyzed, in a number corresponding to the number of analyses which are performed at the same time.

The first motor 51A mounted on a support 52A rotates toothed wheels 53, 54 and 55, and the cams 56 and 58 and associated bushings 57 and 59. A pin 60 rotates through a fork shaped member 61 the body of the substantially cylindrical part of rotating distributor 39 through 90 degrees, so that it is set in correspondence firstly with the inlets and outlets 40 and 41 and secondly with the inlets and outlets 40A and 41A. By means of the cam 58 with a suitable bushing 59, there is actuated a system of valves 17 for two different apertures or different connections for the syringes 22.

A magnet 63 may be energized or switched off, for blocking with a hook 64 the pin 65 which blocks the syringe 22 in the delivery position. In this way when it is not necessary to perform an analysis, the syringe does not aspirate reagent, and does not dispense, but remains in a blocked position.

A second motor 62 operates the double peristaltic pump 50, and a third motor 66 operates the peristaltic pump 11.

A fourth motor 67 actuates the cam 18 and the connecting rod 28 which in turn displaces the guide support 27, which displaces the piston 23 of the syringe 22. The spring 21 restores the piston 23 if it is not blocked by the magnet 63 by means of the hook 64 and pin 65, as above described.

In FIG. 4 there is shown in perspective view the arrangement of the connections of the tubes and the flow of the liquids into the apparatus.

By inserting manually a test tube 68A carrying the sample to be analyzed under the tube 6 and by depressing the microswitch control 7, the peristaltic pump 11 is energized. The liquid to be analyzed is aspirated by means of the tube 6 and enters into the switching valve 12 through the inlet 51 and comes out from 52 for entering into the metering system 13 through the inlet 40, comes out in 41 and comes in again at 40A for a further metering for a further analysis and comes out from 41A. The flow from 40 to 41 may be repeated for a number of times corresponding to the number of analyses which are performed at the same time.

The final outlet 41A communicates with an electronic sensor 15 which detects the presence of the fluid to be analyzed and stops the peristaltic pump 11. This is necessary to avoid wasting the liquid to be analyzed beyond what is necessary for the analysis.

The tube 68 coming from the sensor 15 goes to the peristaltic pump 11 and finally to the drain. A tube 69 is connected with the valve 12 and comes from a bottle of distilled water, and enters into the inlet of switching valve 12 and comes out of outlet 52 at the end of each analysis for washing the whole channel or tube 68 before aspirating a new sample through the tube 6. The syringes 22 are in a number equal to the number of the different reagents necessary for performing the several different analysis with the apparatus. The valve system 17 comprises two connectors for each syringe that is used, a connector 71 for the inlet of the reagent and a connector 72 for the outlet of the reagent.

The connectors 71 are joined with tubes 73 associated to several reagents necessary for performing the analyses. The connectors 72 are joined with the inlets 42, 42A of the metering system by means of tubes 74. The tube 75, on the contrary, carries the washing solution to the microcuvette 35 for washing it after each operational cycle.

An operation or cycle consists in actuating the microswitch 7 that controls the peristatic pump 11. The sample is aspirated through the tube 6, and, through the valve 12 it fills the segments 43 in the rotating distributor 39 goes on the electronic sensor 15 up to the peristatic pump 11 and to the drain through the tube 68.

Once that the sample has been aspirated, the distributor 39 rotates through 90° putting in communication the several inlets 42, 42A with the outlets 44, 44A. Then the syringes 22 are actuated that dispense the reagents through the tubes 73 and send them through the tubes 74 directly to the inlets 42, 42A.

The reagents force the samples contained in the segments 43 together with their reagent into the suitable microcuvettes 35 where the photometric measurement is carried out. At the end of the photometric measurements the multichannel peristaltic pump 50 is energized and the microcuvettes 35 are emptied by means of the tubes 76. One of the syringes 22 is actuated and through the tube 75 a washing solution is forced into the microcuvette 35. The washing solutions are again discharged from the peristaltic pump 50 through the tubes 76. At the same time the distributor 39 is rotated through 90° and through the tube 70 the washing solution is aspirated that goes along the tube 68 washing the metering system for eliminating any contamination between a sample and the next one. The aspiration of the washing solution through the tube 68 is carried out with the peristaltic pump 11.

In FIG. 5 one may see in section a detail of the photometric system 14, carrying the microcuvettes 35 with the quartz windows 77 through which passes the light from the light source 31; the detectors 36, the system for heating the cuvette shown in 78 that utilizes the Peltier effect; the connector 38 for the washing of the cuvette; and the discharge tube 37 associated with each microcuvette.

FIG. 6 is a section carried out along the line VI—VI of FIG. 2 of the valve unit and shows the connectors 71 and 72 that carry the reagents through the tube 73 into the syringes 22 and deliver the reagents through the tubes 74 into the metering system 13.

The present invention has been disclosed with reference to a preferred embodiment, but it will be understood that modifications may be introduced in practice by a person skilled in the art without departing from the scope of the present industrial privilege.

What is claimed is:

1. An automatic multichannel apparatus for performing urgency analyses which comprises, in combination, an arm carrying a tube arranged for aspirating a sample directly from a test tube, a rotating distributor for dividing the sample into several segments correlated with the number of desired analyses comprising a substantially cylindrical body provided with diametral passages, rotatably and sealingly mounted within a housing provided with passages that selectively correspond with said diametral passages according to the angular position of said rotating body, means for aspirating a reagent and transferring this reagent together with a sample segment into a cuvette associated with a photometric measurement unit, and means for the processing of the data of the measurement and for displaying and printing out the results.

2. An apparatus according to claim 1 wherein between said tube carrying arm and said rotating distributor there is provided a switching valve for providing alternate aspiration of sample from said test tube and take up of a washing liquid for cleaning of passages in said distributor.

3. An apparatus according to claim 1 wherein the aspiration of said sample and transfer of said sample segments into cuvettes are obtained by means of a peristaltic pump energized through a microswtich located near said tube carrying arm.

4. An apparatus according to claim 3 wherein between the aspiration of one sample and a succeeding one, said passages of said cylindrical body are cleaned with a washing liquid taken up and sent to the drain by means of a second peristaltic pump.

5. An apparatus according to claim 4 wherein aspiration of reagent and transferring said reagent into said cuvette together with said sample segments is performed by a series of syringes which in the intake stroke takes up the reagent and in the expulsion stroke expels the reagent into the cuvette, and wherein the syringes, the take up peristaltic pump and the second peristaltic pump for washing of the rotating distributor are each actuated by an independent motor.

6. An apparatus according to claim 3 wherein said peristaltic pump provides also for emptying the cuvette after said measurement and printout and sending to a drain the mixture of sample and reagent, and sending to the drain washing liquid which is sent into the cuvette between each measurement.

7. An apparatus according to claim 3 wherein said peristaltic pump is connected to an electronic sensor for detecting the presence of a liquid whereby said pump is stopped as soon as passages in said rotating distributor are filled with the sample to be analyzed.

8. An apparatus according to claim 1 wherein the aspiration of reagent and transferring said reagent into said cuvette together with said sample segments is performed by a series of syringes which in the intake stroke takes up the reagent and in the expulsion stroke expels the reagent into the cuvette.

9. An apparatus according to claim 8 wherein said syringes are actuated by a connecting rod coupled with a cam actuated by a motor.

10. An apparatus according to claim 9 wherein said expulsion stroke of said syringes is effected by a support slidable on guides and drawn by said connecting rod and wherein the intake stroke is effected by means of return springs.

11. An apparatus according to claim 8 wherein the ends of said syringes are connected to a valve unit for switching the steps of take up and expulsion of reagents.

12. An apparatus according to claim 11 wherein a stepwise rotation in increments of 90° of said distributor is obtained by means of a fork shaped element integral with said distributor in which there rotates a pin moved by a cam actuated by a motor which also controls said valve unit connected to the syringes.

13. An apparatus according to claim 8 wherein said syringes may be selectively blocked with a magnet when the analysis associated with a selected syringe is not necessary.

14. An apparatus according to claim 8 wherein one of said syringes has the purpose of taking up a washing solution and sending it into a cuvette after each measurement therein.

* * * * *